(12) United States Patent
Komorowski

(10) Patent No.: US 9,028,879 B2
(45) Date of Patent: May 12, 2015

(54) CHROMIUM COMPLEXES AS ENHANCERS OF BRAIN GLUCOSE TRANSPORTERS

(75) Inventor: James R. Komorowski, Trumbull, CT (US)

(73) Assignee: JDS Therapeutics, LLC, Purchase, NY (US)

( * ) Notice: Subject to any disclaimer, the term of this patent is extended or adjusted under 35 U.S.C. 154(b) by 0 days.

(21) Appl. No.: 13/380,940

(22) PCT Filed: Jun. 30, 2010

(86) PCT No.: PCT/US2010/040679
§ 371 (c)(1),
(2), (4) Date: Dec. 27, 2011

(87) PCT Pub. No.: WO2011/002939
PCT Pub. Date: Jan. 6, 2011

(65) Prior Publication Data
US 2012/0100228 A1    Apr. 26, 2012

Related U.S. Application Data

(60) Provisional application No. 61/222,255, filed on Jul. 1, 2009.

(51) Int. Cl.
| | |
|---|---|
| *A61P 25/28* | (2006.01) |
| *A61P 25/08* | (2006.01) |
| *A61P 5/50* | (2006.01) |
| *A61K 35/30* | (2006.01) |
| *A61P 25/16* | (2006.01) |
| *A61K 31/555* | (2006.01) |
| *A61K 33/24* | (2006.01) |
| *A61P 3/10* | (2006.01) |

(52) U.S. Cl.
CPC ............... *A61K 31/555* (2013.01); *A61K 33/24* (2013.01)

(58) Field of Classification Search
None
See application file for complete search history.

(56) References Cited

U.S. PATENT DOCUMENTS

| | | | |
|---|---|---|---|
| 6,809,115 B2 * | 10/2004 | Katz et al. | 514/505 |
| 2006/0062859 A1 * | 3/2006 | Blum et al. | 424/725 |
| 2007/0231260 A1 | 10/2007 | Zerangue et al. | |
| 2009/0155384 A1 | 6/2009 | Komorowski et al. | |

FOREIGN PATENT DOCUMENTS

| | | |
|---|---|---|
| WO | WO 2008/094939 | 8/2008 |
| WO | WO 2009/009393 | 1/2009 |

OTHER PUBLICATIONS

Rovner, "Alzheimer's Scary Link to Diabetes", Chemical & Engineering News, vol. 87, Issue 20, pp. 42-46, May 18, 2009.*
Simpson et al., "Decreased Concentrations of GLUT1 and GLUT3 Glucose Transporters in the Brains of Patients with Alzheimer's Disease", American Neurological Association, 35, pp. 546-551, 1994.*
International Search Report and Written Opinion dated Aug. 16, 2010 for PCT Application No. PCT/US10/40679.
International Preliminary Report on Patentability dated Nov. 17, 2011 for PCT Application No. PCT/US10/40679.
Harding, Karen L. et al.: "Outcome-based comparison of Ritalin versus food-supplement treated children with AD/HD", Alternative Medicine Review, Thorne Research Inc., Sandpoint, US, vol. 8, No. 3, Aug. 1, 2003, pp. 319-330, XP002565728, ISSN: 1089-5159.
McCarty et al.: "Toward prevention of alzheimers disease—Potential nutraceutical strategies for suppressing the production of amyloid beta peptides", Medical Hypotheses, Eden Press, Penrith, US, vol. 67, No. 4, Jan. 1, 2006, pp. 682-697, XP005541668, ISSN: 0306-9877.
Extended European Search Report and Opinion dated Feb. 27, 2013 for EP Patent Application No. 10 794 738.4.
Komorowski, J. et al.: Journal of Cerebral Blood Flow and Metabolism (2009) 29, S392-S393.

* cited by examiner

*Primary Examiner* — Robert T Crow
*Assistant Examiner* — John P Nguyen
(74) *Attorney, Agent, or Firm* — Knobbe Martens Olson & Bear LLP

(57) ABSTRACT

The embodiments disclosed herein relate to compositions for enhancing brain glucose transporters, such as GLUT1 and GLUT3, and methods of treating and/or preventing diseases or disorders associated with the regulation GLUT1 and GLUT3. Also provided are compositions that include chromium and an agent that targets the brain or the central nervous system. Further provided are improved methods of delivering therapeutic agents that target the brain and/or central nervous system.

8 Claims, 2 Drawing Sheets

HFD Rats: Brain Glut-1 & -3

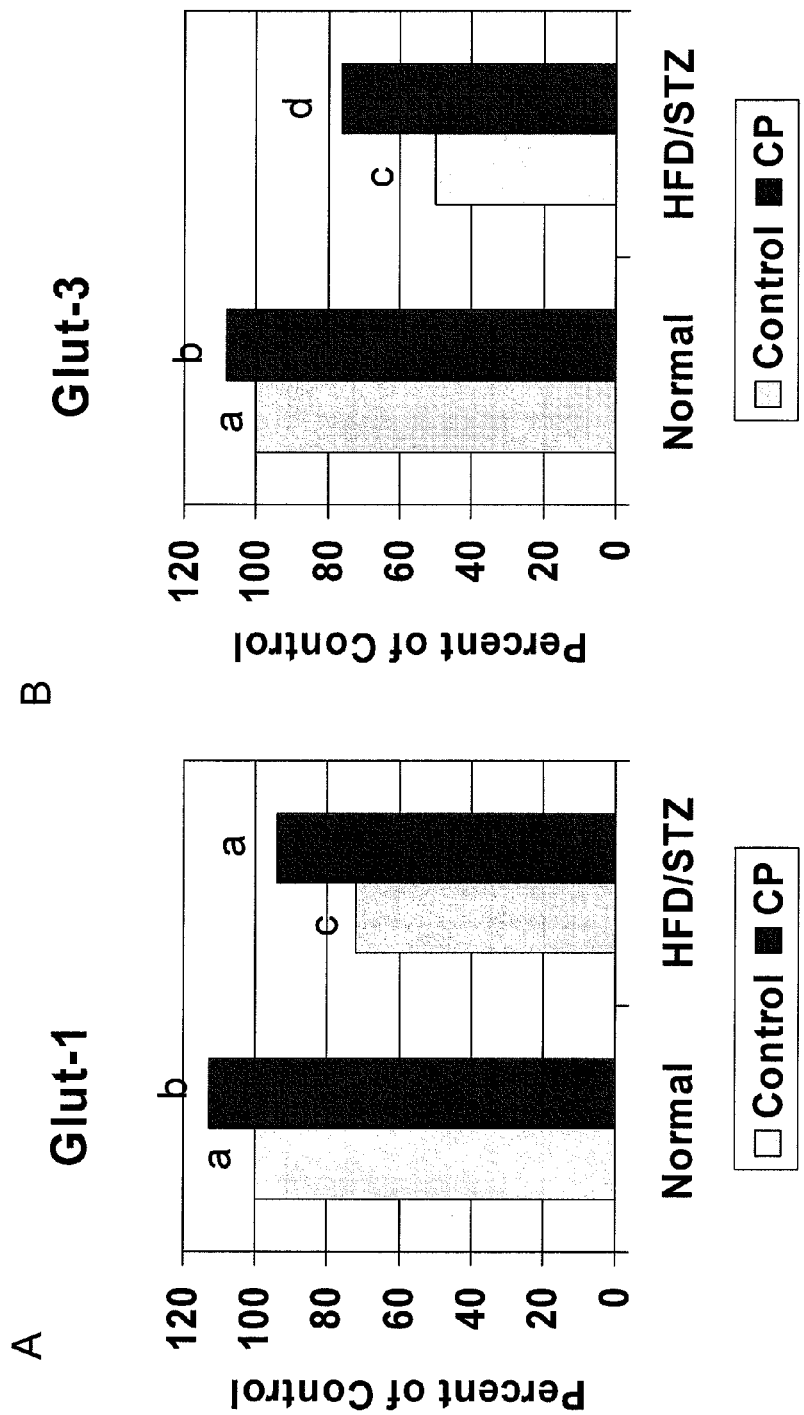

CHROMIUM COMPLEXES AS ENHANCERS OF BRAIN GLUCOSE TRANSPORTERS

CROSS REFERENCE TO RELATED APPLICATIONS

This application claims the benefit and priority to and is a U.S. National Phase Application of PCT International Application Number PCT/US2010/040679, filed on Jun. 30, 2010, designating the United States of America and published in the English language, which is an International Application of and claims the benefit of priority to U.S. Provisional Application No. 61/222,255, filed on Jul. 1, 2009. The disclosures of the above-referenced applications are hereby expressly incorporated by reference in their entireties.

BACKGROUND OF THE INVENTION

1. Field of the Invention

The embodiments disclosed herein relate to uses of chromium for the enhancement of cerebral glucose metabolism, the enhancement of brain glucose transporters, for the treatment and/or prevention of conditions associated with altered cerebral metabolism and/or brain glucose transporter expression. Embodiments disclosed herein also relate to the improved delivery of agents across the blood brain barrier, and improved compositions comprising agents that target the brain and/or central nervous system.

2. Description of the Related Art

Chromium is a nutritionally essential trace element. Chromium is essential for optimal insulin activity in all known insulin-dependent systems (Boyle, et al, *Southern Med. J.* (1977) 70:1449-1453). Insufficient dietary chromium has been linked to both maturity-onset diabetes and to cardiovascular disease.

Chromium functions as a cofactor for insulin. It binds to the insulin receptor and potentiates many, and perhaps all, of its functions. These functions include, but are not limited to, the regulation of carbohydrate and lipid metabolism.

Chromium picolinate is reported to produce modest weight loss and changes in body composition. (Kaats, et al., (1998) *Curr. Ther. Res.* 59:379-388) (Cefalu, (1999) *J. Trace Elem Exp Med* 12:71-83). Chromium is a nutritionally essential trace element. The essentiality of chromium in the diet was established in 1959 by Schwartz, as cited in *Present Knowledge in Nutrition*, page 571, fifth edition (1984, the Nutrition Foundation, Washington, D.C.). Chromium depletion is characterized by the disturbance of glucose, lipid and protein metabolism and by a shortened lifespan. Chromium is essential for optimal insulin activity in all known insulin-dependent systems (Boyle et al., *Southern Med. J.* 70:1449-1453, 1977). Insufficient dietary chromium has been linked to both maturity-onset diabetes and to cardiovascular disease.

The principal energy sources for the body are glucose and fatty acids. Chromium depletion results in biologically ineffective insulin and compromised glucose metabolism. Under these conditions, the body must rely primarily on lipid metabolism to meet its energy requirements, resulting in the production of excessive amounts of acetyl-CoA and ketone bodies. Some of the documented acetyl-CoA is diverted to increased cholesterol biosynthesis, resulting in hypercholesterolemia. Diabetes mellitus is characterized in large part by glycosuria, hypercholesterolemia, and often ketoacidosis. The accelerated atherosclerotic process seen in diabetics is associated with hypercholesterolemia (Boyle et al., supra.).

Dietary supplementation of chromium to normal individuals has been reported to lead to improvements in glucose tolerance, serum lipid concentrations, including high-density lipoprotein cholesterol, insulin and insulin binding (Cefalu et al., (2004) *Diabetes Care* 27(10:2741-51). Supplemental chromium in the trivalent form, e.g. chromic chloride, is associated with improvements of risk factors associated with adult-onset (Type 2) diabetes and cardiovascular disease.

The introduction of inorganic chromium compounds per se into individuals is not particularly beneficial. Chromium must be converted endogenously into an organic complex or must be consumed as a biologically active molecule. Only about 0.5% of ingested inorganic chromium, however, is assimilated into the body. Recommended Daily Allowances, Ninth Revised Edition, The National Academy of Sciences, page 160, 1980. Only 1-2% of most organic chromium compounds are assimilated into the body.

U.S. Pat. No. Re. 33,988 discloses that when selected essential metals, including chromium, are administered to mammals as exogenously synthesized coordination complexes of picolinic acid, they are directly available for absorption without competition from other metals. This patent describes a composition and method for selectively supplementing the essential metals in the human diet and for facilitating absorption of these metals by intestinal cells. These complexes are safe, inexpensive, biocompatible, and easy to produce. These exogenously synthesized essential metal coordination complexes of picolinic acid (pyridine-2-carboxylic acid) have the following structural formula:

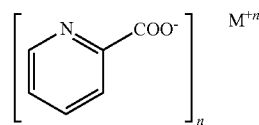

wherein M represents the metallic cation and n is equal to the cation's valence. For example, when M is Cr and n=3, then the compound is chromic tripicolinate. Other chromium picolinate and or chromium histidinate and or chromium complex alone and or in combinations disclosed include chromic monopicolinate and chromic dipicolinate.

The U.S. Recommended Daily Intake (RDI) of chromium is 120 µg. U.S. Pat. No. 5,087,623, the entire contents of which are hereby expressly incorporated herein by reference, describes the administration of chromic tripicolinate for the treatment of adult-onset diabetes in doses ranging from 50 to 500 µg. U.S. Pat. No. 6,329,361, the entire contents of which are hereby expressly incorporated herein by reference, discloses the use of high doses of chromic tripicolinate (providing 1,000-10,000 µg chromium/day) for reducing hyperglycemia and stabilizing the level of serum glucose in humans with Type 2 diabetes. U.S. Pat. Nos. 5,789,401 and 5,929,066, the entire contents of which are hereby expressly incorporated herein by reference, disclose a chromic tripicolinate-biotin composition and its use in lowering blood glucose levels in humans with Type 2 diabetes.

U.S. Pat. Nos. 5,087,623; 5,087,624; and 5,175,156, the entire contents of which are hereby expressly incorporated herein by reference, disclose the use of chromium tripicolinate for supplementing dietary chromium, reducing hyperglycemia and stabilizing serum glucose, increasing lean body mass and reducing body fat, and controlling serum lipid levels, including the lowering of undesirably high serum LDL-cholesterol levels and the raising of serum High Density Lipid (HDL)-cholesterol levels. U.S. Pat. Nos. 4,954,492 and 5,194,615, the entire contents of which are hereby expressly incorporated by reference, describe a related complex, chromic nicotinate, which is also used for supplementing dietary chromium and lowering serum lipid levels.

Nicotinic acid and picolinic acid form coordination complexes with monovalent, divalent and trivalent metal ions and facilitate the absorption of these metals by transporting them across intestinal cells and into the bloodstream. Chromium absorption in rats following oral administration of $CrCl_3$ was facilitated by the non-steroidal anti-inflammatory drugs (NSAIDs) aspirin and indomethacin (Davis et al., (1995) *J. Nutrition Res.* 15:202-210) (Kamath et al., *J Nutrition* (1997) 127:478-482). These drugs inhibit the enzyme cyclooxygenase which converts arachidonic acid to various prostaglandins, resulting in inhibition of intestinal mucus formation and lowering of intestinal pH which facilitates chromium absorption.

U.S. Pat. No. 4,315,927 teaches that when selected essential metals are administered to mammals as exogenously synthesized coordination complexes of picolinic acid, they are directly available for absorption without competition from other metals. These complexes are safe, inexpensive, biocompatible and easy to produce.

The blood-brain barrier (BBB) is a separation of circulating blood and cerebrospinal fluid maintained by the choroid plexus in the central nervous system (CNS). Endothelial cells restrict the diffusion of microscopic objects (e.g., bacteria) and large or hydrophilic molecules into the CSF, while allowing the diffusion of small hydrophobic molecules ($O_2$, hormones, $CO_2$). Cells of the barrier actively transport metabolic products such as glucose across the barrier with specific proteins.

Brain Glucose Transporters

Glucose homeostasis is critical for energy generation, neuronal maintenance, neurogenesis, neurotransmitter regulation, cell survival and synaptic plasticity. It also plays a key role in cognitive function. Facilitative glucose transport is mediated by one or more members of the closely-related glucose transporter (GLUT) family. Thirteen members of the GLUT family have been described thus far. Glucose is the principle energy source for mammalian brain. Delivery of glucose from the blood to the brain requires its transport across the endothelial cells of the blood-brain barrier and across the plasma membranes of neurons and glia, which is mediated by the facilitative glucose transporter proteins. The two primary glucose transporter isoforms which function in cerebral glucose metabolism are GLUT1 and GLUT3. GLUT1 is the primary transporter in the blood-brain barrier, choroid plexus, ependyma, and glia; GLUT3 is the neuronal glucose transporter.

Insulin, a regulator of glucose uptake, is secreted by the pancreas. Insulin allocates glucose to muscle and fat. The hypothalamus-pituitary-adrenal (HPA) axis, the sympathetic nervous system (SNS), and vascular endothelial growth factor allocate glucose to the brain. Feedback pathways both from the brain and from muscle and fat are involved in regulating glucose allocation and exogenous glucose supply. Further, insulin can cross the blood-brain barrier (BBB), reaching neurons and glial cells, and can exert a region-specific effect on glucose metabolism. Increased glucose consumption causes an increase in the net transport of glucose from blood to brain. Thus, insulin indirectly affects the transport without acting on the transport mechanisms. It has been proposed that part of the insulin action may take place in extracerebral tissues via changes of the amino acid balance in the blood (Reagan, et al. (1999) *Am. J. Physiol. Endocrinol. Metab.* 276: E879-E886).

GLUT1, carrying glucose across the blood-brain-barrier, is independent of insulin. Rather, GLUT1 is dependent on potent regulators of blood vessel function like vascular endothelial growth factor (VEGF), a pituitary counter regulatory hormone. GLUT4, carrying glucose across the membranes of muscle and fat cells, depends on insulin. Tissue-specific glucose transporters allocate glucose among organs in order to maintain brain glucose concentrations. HPA-axis overdrive causes metabolic abnormalities such as central adiposity, hyperglycemia, dyslipidemia, and hypertension, that are well known clinical aspects the metabolic syndrome. Overexpression of GLUT1 in skeletal muscle is associated with marked increases in lactate and glycogen due to an increase in basal glucose uptake, and increased glucose flux results in resistance of GLUT4 to activation by insulin and other stimuli, such as hypoxia and contractile activity (Katsumata et al. (1999) *FASEB J.* (11):1405-13).

GLUT3, the neuron-specific glucose transporter, is solely responsible for the delivery of glucose into neurons in the central nervous system. GLUT3 mRNA is widely expressed in the brain, including the pyramidal neurons of the hippocampus and the granule neurons of the dentate gyrus.

Brain-specific kinases 1 and 2 (BRSK1/2) are AMP-activated protein kinase (AMPK)-related kinases that are highly expressed in mammalian forebrain. The activation of AMPK plays an important, albeit not an exclusive, role in the induction of recruitment of the insulin-dependent glucose transporter found in skeletal muscle, GLUT4, to the plasma membrane. The ability of AMPK to stimulate GLUT4 translocation to the plasma membrane in skeletal muscle occurs via a mechanism distinct from that stimulated by insulin since together insulin and AMPK effects are additive. In addition to its role in the regulation of GLUT4, data suggest that AMPK regulates glucose transport through GLUT1.

Altered glucose metabolism in the brain is associated with various disease states, including but not limited to Alzheimer's disease, Huntington's Disease, epilepsy, ischemia, amnesia, and traumatic brain injury. Glucose transporter expression is believed to be related to altered glucose metabolism. Chronic hyperglycemia downregulates GLUT(1) and GLUT(3) expression at both mRNA and protein levels in the brain, which is not due to the decrease of the density of microvessels (Hou, et al. (2007) *Chin Med J (Engl)*. 120(19): 1704-1709). The downregulation of GLUT1 and GLUT 3 expression might be the adaptive reaction of the body to prevent excessive glucose entering the cell that may lead to cell damage. Studies suggest that chronic stress produces molecular, morphological, and ultrastructural changes in the hippocampus that are accompanied by cognitive deficits. Further, in insulin resistance, dementia, and cognitive impairment, and Alzheimer's disease, there is a reduced sensitivity to insulin resulting in hyperinsulinemia. Toxic levels of insulin negatively influence neuronal function and survival, and elevation of peripheral insulin concentration acutely increases its cerebrospinal fluid (CSF) concentration. Peripheral hyperinsulinemia correlates with an abnormal removal of the amyloid beta peptide (Abeta) and an increase of tau hyperphosphorylation as a result of augmented cdk5 and GSK3beta activities. This leads to cellular cascades that trigger a neurodegenerative phenotype and decline in cognitive function.

In Alzheimer's Disease, glucose metabolism is decreased and is associated with decreased amounts of GLUT1 protein in cerebral microvessels in the frontal cortex and hippocampus, the regions most affected (Kalaria, et al., (1989) *J. Neu-* rochem. 53:1083-1088). Likewise, GLUT3 levels have been reported to be reduced in the brains of patients with Alzheimer's Disease (Simpson, et al. (1994) *Ann. Neurol.*, 35:546-551).

Huntington's disease is a neurodegenerative disorder. Early stages of the disease are characterized by subtle changes in personality, cognition, or physical skills. The most characteristic initial physical symptoms is chorea, characterized by jerky, random, and uncontrollable movements. Chorea is often initially exhibited as general restlessness, small unintentionally initiated or uncompleted motions, uncoordination, or slowed saccadic eye movements. Symptoms such as rigidity, repetitive motions or abnormal posturing appear as the disorder progresses. These symptoms are regarded as the onset stage of the disease, and gradually become the dominant physical symptoms. Juvenile Huntington's Disease differs from these symptoms, in that it generally progresses faster and chorea is exhibited briefly, if at all, with rigidity being the dominant symptom. Additionally, seizures are a common symptom of Juvenile Huntington's Disease. In Huntington's disease, GLUT 1 and GLUT3 levels are decreased in the caudate portion of the brain. (Gamberino, et al. (1994) *J. Neurochem.* 63:1392-1397). Decreases in caudate glucose metabolism have been reported in subjects with both symptomatic and clinically asymptomatic subjects at risk for Huntington's Disease. (Mazziotta, et al. (1987) *New England J. Med.* 316:357-362).

Glucose transport is also decreased in the human epileptic brain, due at least in part to decreased expression of GLUT1 at the blood brain barrier endothelium (Cornford, et al. (1998) *Ann. Neurol.* 43:801-808) (Cornford et al. (1998) *J. Neuropathol. Exp. Neurol.* 54:842-851).

Idiopathic epilepsy has a greater incidence amongst the type 1 diabetic population than the greater population (Developmental Medicine & Child Neurology 2003; 45:4:262-268). Meanings inferred from the results could be interpreted in several ways. Diabetes could be partly responsible for idiopathic generalized epilepsy, or the two conditions could have different ages of onset. Metabolic abnormalities including hyperglycemia, mild hyperosmolality and hyponatremia contribute to the development of epilepsiapartialis continua in an area of focal brain damage. Occipital seizures and hemianopsia can be caused by hyperglycemia and may be accompanied by special MRI and VEP findings. The increased incidence of seizure and delayed neuronal damage resulting from pre-ischemic hyperglycemia corresponds with corticosterone levels rather than with glucose levels and suggests that corticosterone has a greater prognostic value than glucose in predicting cerebral ischemic damage.

GLUT1 deficiency syndrome is a disorder that primarily affects the brain. Affected individuals generally have seizures beginning in the first few months of life. Babies with GLUT1 deficiency syndrome have a normal head size at birth, but growth of the brain and skull is often slow, in severe cases resulting in an abnormally small head size (microcephaly). Subjects with GLUT1 deficiency syndrome often exhibit developmental delay or intellectual disability. GLUT1 deficiency syndrome is also associated with other neurological problems, such as stiffness caused by abnormal tensing of the muscles (spasticity), difficulty in coordinating movements (ataxia), and speech difficulties (dysarthria). Some experience episodes of confusion, lack of energy (lethargy), headaches, muscle twitches (myoclonus), or involuntary irregular eye movements, particularly before meals.

The Blood Brain Barrier

The blood-brain barrier (BBB) remains a major obstacle to the successful delivery of drugs to treat central nervous system (CNS) disorders, brain tumors, and the like. Overcoming the difficulty of delivering therapeutic agents to specific regions of the brain presents a major challenge to treatment of most brain disorders, and disorders affecting the CNS. In its neuroprotective role, the blood-brain barrier functions to hinder the delivery of many potentially important diagnostic and therapeutic agents to the brain. Therapeutic molecules and genes that might otherwise be effective in diagnosis and therapy do not cross the BBB in adequate amounts.

Several approaches have been taken in order to facilitate delivery of therapeutics across the BBB, including (1) improving or increasing the lipophilicity of the drug, to increase the molecule's membrane permeability; (2) making the drug more cationic; (2) chemically modifying the drug to target an uptake mechanism; and (3) conjugating the drug to a molecular chaperone. Common methods include lipo-conjugates, glycol-conjugates, and glycolipo-conjugates. Glycosylation has shown potential as a methodology for improving drug delivery across the BBB.

Recently, modification of drugs with sugar chains has been studied as a strategy to facilitate transport of drugs across the BBB, via the GLUT1 transporter. For example, Kriss et al. ((2000) *Tetrahedron-Asymmetr.*, 11:9-25) coupled β-D-glucose to the opioid peptide molecule. The glycopeptides were shown to penetrate into the brain. Bilsky et al. ((2000) *J. Med. Chem.* 43:2586-2590), showed that attaching simple sugars to enkephalins resulted in an increase in their penetration into the BBB. Bourasset et al. ((2003) *J. Neurochem.* 86:1564-1567) demonstrated the morphine uptake in the brain was increased in the presence of D-glucose.

There is a need for improved therapies for disorders and diseases associated with altered brain glucose levels and/or metabolism. There is also a need for the more efficient delivery of CNS therapeutics across the blood brain barrier.

SUMMARY OF THE INVENTION

Embodiments provided herein relate to unexpected finding that chromium supplementation enhances the brain glucose transporters. Embodiments disclosed herein relate to compositions and methods for enhancing glucose transporters in the brain of a subject in need thereof.

In some embodiments, provided herein are methods for enhancing brain glucose transporters that include identifying a subject in need of increased glucose transport in the brain; and administering to the subject an amount of chromium effective to increase the levels of GLUT1 or GLUT3 in the brain. In some embodiments, the subject has a disease or disorder associated with decreased level of glucose transporters in the brain.

In some embodiments, the disease or disorder can be, for example, Alzheimer's disease, dementia, mild cognitive impairment (MCI), attention deficit hyperactive disorder (ADHD), Huntington's Disease, epilepsy, Parkinson's Disease, or a disease characterized by abnormally low levels of GLUT1 or GLUT3 in the brain.

Embodiments provided herein also relate to compositions that include an agent that targets the brain or central nervous system (CNS) and chromium. The agent that targets the brain and/or central nervous system can be selected from the group consisting of a cholinesterase inhibitor, an antidepressant, an antipsychotic, an anxiolytic, a sleep aid, and chemotherapeutic agent. In some embodiments, the chromium is a chromium complex.

Embodiments provided herein also relate to methods for facilitating transport of a drug across the blood brain barrier. In some embodiments, a subject can be identified as being in need of transport of an agent across the blood brain barrier. The subject can be administered the agent and chromium. In some embodiments, the chromium and the agent are administered substantially simultaneously. For example, in some embodiments, the subject is administered a composition that includes both the agent and the chromium. In some embodiments, the agent can be selected from the group consisting of: cholinesterase inhibitor, an antidepressant, an antipsychotic, an anxiolytic, a sleep aid and chemotherapeutic agent. In some embodiments, the subject can be pre-treated by administering chromium, and subsequently administered a compound or agent that is glycosylated as described herein. For example, in some embodiments, the subject can be administered chromium 1, 2, 3, 4, 5, 6, 7, 8, 9, 10, 15, or 20 times daily, for a period of days, weeks, months, or longer, prior to being administered a glycosylated agent.

Also provided are uses of compositions that include chromium in the manufacture of a medicament to increase brain glucose transporters, and/or to treat and/or prevent diseases or disorders associated with altered cerebral glucose metabolism, or altered brain glucose transport function.

BRIEF DESCRIPTION OF THE DRAWINGS

FIGS. 2A and 2B are bar graphs showing the percent of GLUT1 (FIG. 2A) and GLUT3 (FIG. 2B) protein expression in brain tissue in rats relative to control. Rats were fed either a standard diet, or a high fat diet, in conjunction with streptozotocin (STZ) treatment. Rats received either no chromium (control) or chromium picolinate (CP), as described in Example 2.

DETAILED DESCRIPTION OF THE PREFERRED EMBODIMENT

Figure 1:
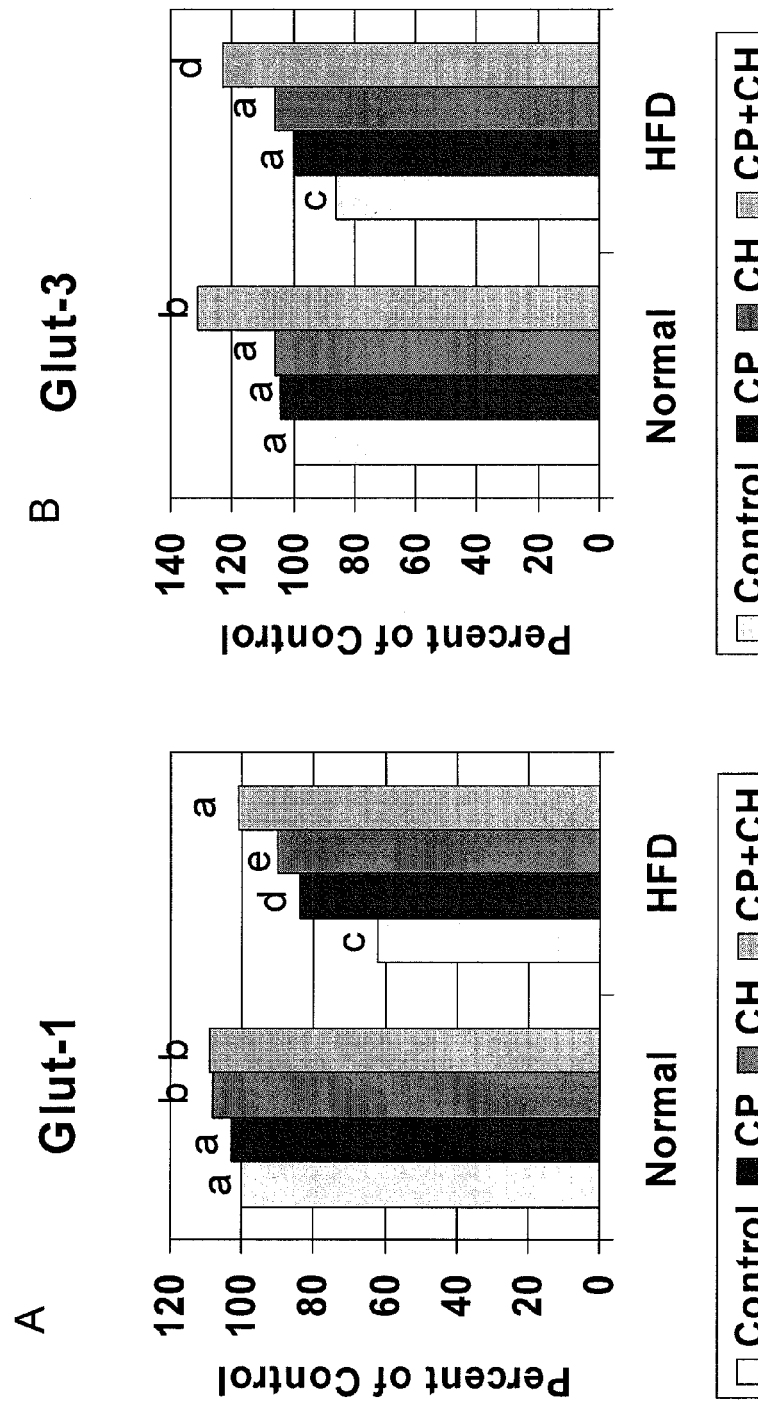
FIGS. 1A and 1B are bar graphs showing the percent of GLUT1 (FIG. 1A) and GLUT3 (FIG. 1B) protein expression in brain tissue in rats relative to control. Rats were fed either a standard diet, or a high fat diet. Rats received no chromium (control), chromium picolinate (CP), chromium histidinate (CH) or a combination of chromium picolinate and chromium histidinate (CP+CH), as described in Example 1.

The embodiments disclosed herein are based, in part, on Applicants' surprising discovery that chromium up-regulates GLUT1 and GLUT3 levels in brain tissue. This finding is particularly unexpected in view of the state of the art, which suggests that neither GLUT1 nor GLUT3 is regulated by insulin, for which chromium is a cofactor. As an up-regulator of GLUT1 and GLUT3 in brain tissue, Applicants have discovered that chromium and chromium complexes can be advantageously be used to treat diseases and conditions associated with altered cerebral glucose metabolism, and, additionally, to facilitate the transport of drugs and compounds that use GLUT1 and/or GLUT3 to cross the blood brain barrier. Provided herein are compositions for increasing GLUT1 and/or GLUT3 in subjects in need thereof, including subjects with conditions associated with decreased cerebral glucose metabolism and/or uptake, as well as compositions and methods for increasing transport of compounds across the blood brain barrier.

Enhancement of Brain Glucose Transporters

Some embodiments provide methods of enhancing brain glucose transporters in a subject in need thereof. As used herein, the term "brain glucose transporter," (GLUT) refers to a protein involved in facilitative glucose transport in the brain, either now known or discovered in the future. In preferred embodiments, the methods disclosed herein enhance the levels of GLUT1 or GLUT3 in the subject. Enhancement of the levels of GLUT1 or GLUT3 refers to an increase of GLUT1 or GLUT3 transcription products and/or protein expression products in brain tissue, when compared to a baseline (i.e., before treatment with chromium) level. The enhancement of GLUT1 and GLUT3 levels in the subject can be independent of insulin, and in some embodiments is observed in insulin resistant subjects and/or in subjects that have hyperinsulinemia In some embodiments, the subject can be a mammal. For example, in some embodiments, the subject can be selected from the group consisting of mice, rats, rabbits, guinea pigs, dogs, cats, sheep, goats, cows, primates, such as monkeys, chimpanzees, and apes, and humans. Preferably, the subject is a human.

In some embodiments, the subject can be identified as being in need of increased levels of GLUT transporters, such as GLUT1 or GLUT3. In some embodiments, the subject can be identified as having or being at risk of developing a disease or condition associated with altered cerebral glucose metabolism. For example, in some embodiments, the subject can be identified as having, or being at risk for developing one or more diseases or conditions associated with altered GLUT1 and/or GLUT3 levels. For example, in some embodiments, the subject can be identified as having, or at risk of developing dementia and/or cognitive impairment, including mild cognitive impairment (MCI), mild dementia, moderate dementia, or severe dementia. Various types of dementia and/or cognitive impairment can be assessed by routine methods known to those skilled in the art. Certain measurements of atrophy (shrinkage) or decreased metabolism on images of the brain (PET or MRI scans) increase the chances of developing dementia in the future. The medical evaluation of the dementia can include a thorough exploration of the memory complaints, including reports of memory loss, such as what type of information is being forgotten and when, the duration of the problem, and whether other cognitive complaints are occurring (problems with organization, planning, visuospatial abilities, etc). Assessment of dementia and/or cognitive impairment can include the following non-limiting tests: blood and/or urine tests, memory tests, problem solving tests, counting tests, language tests, brain computed tomography (CT) and/or magnetic resonance imaging (MRI) scans, single photon emission computed tomography (SPECT), PET scans, neurological tests, and the like.

In some embodiments, the subject can be identified as having GLUT1 deficiency syndrome. For example, in some embodiments, the subject can be identified as having an SLC2A1 mutation, as identified by genetic testing. Subjects identified as having an SLC2A1 mutation can exhibit reduced function of the glucose transporter protein type 1 produced from one copy of the gene in each cell. This is sufficient for maintenance of neuronal energy supply, motor abilities, learning and memory, and feeding behavior. Reduced transporter function lessens the availability of glucose, resulting in the signs and symptoms of GLUT1 deficiency syndrome.

In some embodiments, the subject can have, or be at risk of developing Alzheimer's Disease (AD). Individuals having or at risk of developing Alzheimer's disease can be identified using conventional methods, including but not limited to PET scans, genetic screening, e.g., for ApoE alleles, genetic mutations associated with familial AD (FAD), and the like.

In some embodiments, the subject can have, or be at risk of developing attention deficit hyperactive disorder (ADHD). Subjects having or at risk of developing ADHD can be identified using routine methods known in the art, including but not limited to DSM-IV criteria, ICD-10 criteria, and the like.

In some embodiments, the subject can have, or be at risk of developing depression, e.g., major depression with associated cognitive impairment.

In some embodiments, the subject can be identified as having dementia and/or cognitive impairment associated with insulin resistance. In some embodiments, the subject can be identified as having cognitive impairment associated with hypoglycemia. Conventional tests for dementia and or cognitive impairment associated with insulin resistance include, but are not limited to the Mini-Mental State Examination (MMSE). (Folstein, et al. (1975) *J Psychiatr Res.,* 12:189-198). Indicators of insulin resistance include, but are not limited to: (1) fasting blood insulin level, determined by a commercially available radioimmunoassay kit (coefficient of variation, mean±SD, 3.2%±0.3%; cross-reactivity with 0.3% proinsulin; Sorin Biomedical, Milan, Italy); (2) IR index, estimated using the Homeostasis Model Assessment of Insulin Resistance (HOMA-IR) (Matthews, et al. (1985) *Diabetologia* 28:412-419): IR=[fasting glucose level (millimoles per liter)]×[fasting insulin level (microunits per milliliter)]/22.5; and (3) insulin sensitivity index, computed with the Quantitative Insulin Sensitivity Check Index (QUICKI) (Katz, et al. (2000), *J Clin Endocrinol Metab.:* 85:2402-2410): insulin sensitivity=1/[log fasting insulin level (microunits per milliliter)]+[log fasting glucose level (milligrams per deciliter)].

In one embodiment, the subject is identified as having or being at risk of developing a cognitive condition associated with reduced brain insulin levels, and/or having or being at risk of developing a cognitive condition associated with insulin excess. In some embodiments, the subject is identified as being in need of normalization of insulin levels, such as brain insulin levels.

The identification step can be performed by a medical practitioner, such as a physician, a nurse, a nurse practitioner, or the like. In some embodiments, however, the identification step is performed by the subject, i.e., self-evaluation.

In some embodiments, the chromium can be administered for the purpose of increasing the levels of brain glucose transporters, such as GLUT1 and/or GLUT3. In some embodiments, the chromium can be administered for the purpose of increasing cerebral glucose metabolism. In some embodiments, the chromium can be administered for the purpose of increasing brain glucose levels. For example, in some embodiments, the subjects disclosed herein can be advised that the chromium can increase levels of brain glucose transporters, and/or increase cerebral glucose metabolism.

In some embodiments, the methods disclosed herein include the step of administering chromium to the subject. The chromium can be provided in any form, e.g., $CrCl_3$, a chromium complex, or the like. Non-limiting examples of chromium complexes useful in the embodiments disclosed herein include, but are not limited to dinicotinate chromium complexes having a carboxylate ligand as a third ligand. The third ligand can be selected from the group consisting of alanine, aspartic acid, asparagine, arginine, cysteine, glutamic acid, glutamine, histidine, isoleucine, lysine, leucine, methionine, phenylalanine, proline, serine, threonine, tyrosine, tryptophan, valine, gallic acid, cinnamic acid, hydroxycitric acid, and 5-hydroxytryptophan. The third ligand can be a simple carboxylate (e.g., propionate), a carboxylate having other coordinating functionality (e.g., amino acids or hydroxy-acids), and/or a carboxylate having pi electrons available for potential secondary bonding to chromium through chromium's d-orbitals (e.g., tyrosine or tryptophan) or glutamate, cysteine, aspartate, tryptophan, cinnamate, and the like. Other chromium complexes useful in the embodiments disclosed herein include complexes of chromium and one, two, or three ligands selected from the group consisting of glycine, alanine, aspartic acid, asparagines, arginine, cysteine, glutamic acid, glutamine, histidine, isoleucine, lysine, leucine, methionine, phenylalanine, praline, serine, threonine, tyrosine, tryptophan, valine, gallic acid, cinnamic acid, hydroxycitric acid, 5-hydroxytrytophan, and nicotinic acid.

Some chromium complexes useful in the embodiments disclosed herein include, but are not limited to, the following: Chromium histidinate Chromium trihistidinate, and Chromium polyhistidinate, Chromium dinicocysteinate; Chromium dinicotinate tryptophan; Chromium dinicotinate tyrosine; Chromium dinicotinate hydroxycitrate; Chromium dinicotinate cinnamate; Chromium dinicotinate gallate; Chromium dinicotinate 5-hydroxytryptophan; Chromium dinicotinate aspartate; Chromium dinicotinate glutamate; Chromium dinicotinate arginate; Chromium tris(tryptophan); Chromium nicotinate, Chromium picolinate, Chromium triphenylalanine; Chromium tris(tyrosine); Chromium tris(hydroxycitrate); Chromium tris(5-hydroxytryptophan); Chromium tris(cinnamate); Chromium tris(gallate); Chromium complexes disclosed herein are chromium having three different carboxylate ligands. By varying ligands from nicotinic acid, glutamate, cysteinate, aspartate, argininate, tyrosine and tryptophan, at least 30 possible chromium complexes can be produced.

In various cases, the ligand(s) has/have the ability to bond to chromium via its carboxylate functional group as well as through pi electron-d orbital interaction. This secondary interaction between the ligand and chromium can increase the bioavailability and absorption of chromium.

In some embodiments, the chromium complexes can be complexes of trivalent chromium and at least one and no more than three tyrosine or tryptophan ligands. In specific embodiments, the present invention provides chromium complexes such as chromium (III) tris(tryptophan) and chromium (III) tris(tyrosine).

In some embodiments, the chromium complexes can be complexes of trivalent chromium and one or more compounds extracted from plants. Non-limiting examples of plants from which these compounds can be extracted include plants such as genus *Garcinia, Groffonia simplicifolia,* cinnamon bark, gallnuts, sumac, witch hazel, tea leaves, and oak bark. For example, in some embodiments, chromium can be provided in the form of chromium hydroxycitrate, chromium hydroxytryptophan, chromium cinnamate, and chromium gallate.

Preferably, the chromium is provided as a combination of chromium picolinate and chromium histidinate, or as a combination of chromium nicotinate and chromium histidinate.

The chromium can be provided to the subject in a therapeutically effective amount. In some embodiments, a therapeutically effective amount refers to an amount effective to enhance or increase GLUT1 and/or GLUT3 levels in the brain, and/or to increase brain insulin levels. The term "therapeutically effective amount" as used herein refers to that amount of a composition being administered which will relieve to some extent one or more of the signs or symptoms of a disease or condition associated with altered GLUT1 and/or GLUT3 expression. For example, the patient can be administered an amount of chromium effective to improve or maintain symptoms of cognitive impairment, Alzheimer's disease, Parkinson's disease, ADHD, Huntington's disease, epilepsy, GLUT1 deficiency syndrome, and the like. In some embodiments, chromium can be provided to the subject in an amount between about 0.001 µg to about 10 g, preferably per day. For example, the amount of chromium can be 0.001 µg, 0.01 µg, 0.1 µg, 0.2 µg, 0.3 µg, 0.4 µg, 0.5 µg, 0.6 µg, 0.7 µg, 0.8 µg, 0.9 µg, 1 µg, 2 µg, 3 µg, 4 µg, 5 µg, 6 µg, 7 µg, 8 µg, 9 µg, 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any range or amount in between any two of the preceding values.

In some embodiments, the chromium is administered to the subject 1 time, 2 times, 3 times, 4 times 5 times, 6 times, 7 times, 8 times, 9 times, 10 times, or more, per day, for a period of time, such as 1 day, 2 days, 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 2 months, 3 months, 4 months, 5 months, 6 months, 7 months, 8 months, 9 months, 10 months, 11 months, 1 year, or more, or any amount of time in between the preceding values.

The enhancement or increase in GLUT1 or GLUT3 can, in some embodiments, be detected. For example, conventional methods can be used to determine the amount of glucose metabolism or activity of the brain. An enhancement or increase can refer to any positive change, e.g., 2%, 3%, 4%, 5%, 6%, 7%, 8%, 9%, 10%, 12%, 15%, 20%, 25%, 30%, 35%, 40%, 45%, 50%, 55%, 60%, 65%, 70%, 75%, 80%, 85%, 90%, 95%, 100%, 150%, or more of baseline, or any range or amount in between any two of the preceding values.

In some embodiments, the amount of chromium is effective to decrease the symptoms associated with the conditions described herein by about 2%, 5%, 10%, 15%, 20%, 25%, 30%, 40%, 50%, 60%, 70%, 80%, 90%, 100%, or more.

In some embodiments, the subject can be administered a second agent, in addition to and in conjunction with the chromium. In some embodiments, the second agent can be a chelating agent. For example, in some embodiments, the subject can be administered D or L amino acids, tri amino acid formulae including but not limited to, triphenylalanine, tri histidine, tri arginine, picolinic acid, nicotinic acid, or both picolinic acid and nicotinic acid. Chelating agents such as histidine, picolinic acid and nicotinic acid are available from many commercial sources, including Sigma-Aldrich (St. Louis, Mo.) (picolinic acid; catalog No. P5503; nicotinic acid; catalog No. PN4126). Preferably, the ratio of the chromium complex to the chelating agent administered is from about 10:1 to about 1:10 (w/w), more preferably from about 5:1 to about 1:5 (w/w). Alternatively, the molar ratio of chromium complex to the uncomplexed chelating agent can be preferably 1:1, and may be from about 5:1 to about 1:10. More than one chelating agent, e.g, both nicotinic and picolinic acid can be included in the compositions disclosed herein, or administered to subject in the methods described herein.

In some embodiments, the second agent can be a therapeutic for the treatment of impaired cognitive function, such as cholinesterase inhibitors, memanitine, vitamin E supplementation, phospholipid supplementation, omega-3 fatty acid supplementation. Other phospholipids and omega-3 fatty acids may also be used in combination with a chromium picolinate complex. Other phospholipids include phosphatidyl ethanolamine, phosphatidylglycerol and phosphatidylcholine (lecithin). Other omega-3 fatty acids include α-linoleic acid (ALA).

In some embodiments, the second agent can be a therapeutic agent used to treat a condition or disorder or symptoms associated therewith associated with altered cerebral glucose metabolism, such as altered GLUT1 and/or GLUT3 expression or activity. For example, non-limiting examples of therapeutic agents include cholinesterase inhibitors, such as donepezil (ARICEPT®); rivastigmine (EXELON®); galantamine (RAZADYNE®); memantine (NAMENDA®); tacrine (COGNEX®); amantiadine; slegiline; levadopa/carbidopa; levodopa/benserazide; entacapone; tolcapone; bromocriptine; pergolide; ropinirole; cabergoline; apomorphine; lisuride; biperiden HCl (AKINETON®); Benzotropine mesylate (COGENTIN®); Procyclidine, trihexyphenidyl; Tetrabenazine (XENAZINE®); clonazepam (KLONOPINAND®); clozapine (CLOZARIL®); nortriptyline (PAMELOR®); Lithium (ESKALITHAND®); selective serotonin reuptake inhibitors, such as Citalopram escitalopram (LEXAPRO®), fluvoxamine (LUVOX®), paroxextine (PAXIL®), fluoxetine (PROZAC®), and sertraline (ZOLOFT®), tricyclic antidepressants, such as Amitriptyline, desipramine, nortriptyline, duloxetine, desvenlafaxine, mirtazepine; monoamine oxidase inhibitors (MAOI's), such as phenelzine (NARDIL®), tranylcypromine (PARNATE®); venlafaxine, buproprioin (WELLBUTRIN®); atypical antipsychotics such as amisulpride, Ariprpazole, asenapine, iloperidone, melperone, olanzapine, paliperidone, perosprione, quetipaine, risperidone, sertindole, sulpride, ziprasizone; antipsychotics such as chlorpromazine, flupehazine, haloperidol, moindone, thiothixene, thioridazine, trifluoperazine, loxaine, perphenazine, prochlorperazine, pimozide, auclopenthixol, Ritalin, methyline, metadata, focalin, dayrana, concerta, adderall, Dexedrine, vyvanse, clonidine (CATAPRES®), guanfacine (TENEX®); atomoxetine (STRATTERA®), memanitine, vitamin E, a phospholipid or an omega-3 fatty acid and the like, or any combination thereof.

In some embodiments, chromium can be administered to a subject taking an antispychotic or antineurotic agent. In some embodiments, the chromium can minimize side effects associated with antipsychotic and/or antineurotic therapeutics, by administering a therapeutically effective amount the antipsychotic agent and/or antineurotic agent in combination with approximately about 0.001 mg/day to about 10 mg/day of chromium. The side effects can include, for example, weight gain, hyperglycemia, hypertriglyceridemia, hypercholesterolemia, increased adiposity, negative impact on cognitive function(s), and combinations thereof.

In some embodiments, the chromium and the second agent are provided in a single composition. In some embodiments, the chromium and the second agent are provided in separate compositions. In embodiments wherein the chromium and the second agent are provided in separate compositions, the agents can be administered simultaneously, or substantially simultaneously. Substantially simultaneously refers to within 1 minute, 5 minutes, 10 minutes 15 minutes, 20 minutes 25 minutes, 30 minutes, 1 hour, 2 hours, 3 hours, 5 hours, 10 hours, 15 hours, or 24 hours. In embodiments wherein the chromium and second agent are provided in separate compositions, the chromium and the second agent can be administered sequentially in either order.

In some embodiments, symptoms or conditions associated with the deficiency of GLUT1 and/or GLUT3 can be measured, following the treatment with chromium.

The administration of the compositions disclosed herein can be by any of the methods of administration described herein or by delivery methods known by one of skill in the art. The compositions may be administered orally, through parenteral nutrition, e.g., feeding tube or intravenously, and through other known means.

For oral administration, the compositions disclosed herein can be provided as a tablet, aqueous or oil suspension, dispersible powder or granule, emulsion, hard or soft capsule, syrup, elixir, or beverage. Compositions intended for oral use can be prepared according to any method known in the art for the manufacture of pharmaceutically acceptable compositions and such compositions may contain one or more of the following agents: sweeteners, flavoring agents, coloring agents and preservatives. The sweetening and flavoring agents will increase the palatability of the preparation. Tablets containing chromium complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. Aqueous suspensions can contain the chromium complex of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions can be formulated by suspending the active ingredient in a vegetable oil, such as arachis oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, can also be present.

Syrups and elixirs can be formulated with sweetening agents, such as glycerol, sorbitol or sucrose. Such formulations can also contain a demulcent, a preservative, a flavoring or a coloring agent.

The chromium preparations for parenteral administration can be in the form of a sterile injectable preparation, such as a sterile injectable aqueous or oleaginous suspension. This suspension can be formulated according to methods well known in the art using suitable dispersing or wetting agents and suspending agents. The sterile injectable preparation can also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils can be employed conventionally as a solvent or suspending medium. For this purpose, any bland fixed oil can be employed including synthetic mono or diglycerides. In addition, fatty acids such as oleic acid can likewise be used in the preparation of injectable preparations.

The compositions can also be in the form of oil-in-water emulsions. The oily phase can be a vegetable oil, such as olive oil or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

It will be appreciated by the skilled artisan that the amount of chromium or chromium complex that can be combined with the carrier material to produce a single dosage form will vary depending upon the host treated and the particular mode of administration.

When administered to a mammal, e.g., to an animal for veterinary use or for improvement of livestock, or to a human for therapeutic use, the compositions disclosed herein are administered in isolated form or as the isolated form in a therapeutic composition. As used herein, "isolated" means that the compositions disclosed herein are separated from other components of either (a) a natural source, such as a plant or cell or food, preferably bacterial culture, or (b) a synthetic organic chemical reaction mixture. Preferably, via conventional techniques, the compositions disclosed herein are purified. As used herein, "purified" means that when isolated, the isolate contains at least 95%, preferably at least 98% of the composition.

In some embodiments, the compositions disclosed herein are provided to the subject orally. In other embodiments, the compositions disclosed herein are provided by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems useful in the methods disclosed herein include for example, encapsulation in liposomes, microparticles, microcapsules, capsules, etc., and can be used to administer a compound of the invention. In certain embodiments, more than one composition disclosed herein is administered to an individual.

Other modes of administration useful in the methods include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the professional, and will depend in-part upon the site of the condition to be treated. In most instances, administration will result in the release of the compositions disclosed herein into the bloodstream.

In specific embodiments, it can be desirable to administer one or more compositions disclosed herein locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue In certain embodiments, for example, for the treatment of Alzheimer's disease, it may be desirable to introduce one or more compositions disclosed herein into the central nervous system by any suitable route, including intraventricular, intrathecal or epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compositions disclosed herein can be formulated as a suppository, with traditional binders and vehicles such as triglycerides.

Preferably, the compositions disclosed herein are formulated with a pharmaceutically acceptable vehicle. As used herein, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compositions of the invention and pharmaceutically acceptable vehicles are preferably sterile. Water is a preferred vehicle when the compositions of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use.

In some embodiments, the compositions disclosed herein are formulated for oral delivery, for example in the form of tablets, lozenges, aqueous or oily suspensions, granules, powders, emulsions, capsules, syrups, or elixirs. Compounds and compositions described herein for oral delivery can also be formulated in foods and food mixes. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compounds and compositions described herein. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, etc. Such vehicles are preferably of pharmaceutical grade.

In some embodiments, the compositions described herein can be in the form of nutraceutical packs not limited to functional foods, beverages, bars, dietary supplements, capsules, powder form or gelatin form, pharmaceutical packs or kits comprising one or more containers filled with one or more compositions disclosed herein. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the nutraceuticals can be in the form of a kit that contains more than one compound described herein. In some embodiments, the kit can include information that advises individuals that the chromium can increase brain glucose transporter levels, e.g., GLUT1 and/or GLUT3 levels. The kit can include information that advises individuals that the chromium can increase cerebral glucose metabolism, and/or that the chromium can decrease brain insulin resistance. The kit can also include information that advises individuals that the chromium can be beneficial in ameliorating or preventing cognitive impairment, and/or symptoms associated with a disease or disorder associated with decreased cerebral glucose metabolism and/or decreased brain glucose transporter levels.

The compositions disclosed herein can be assayed in vitro and in vivo, for the desired therapeutic or prophylactic activity, prior to use in humans. For example, in vitro assays can be used to determine whether administration of a specific compound described herein or a combination of compositions disclosed herein is preferred for improving symptoms associated with altered GLUT1 and/or GLUT3 levels, altered cerebral glucose metabolism, or any disease or condition disclosed herein. The compositions disclosed herein also be demonstrated to be effective and safe using animal model systems.

Methods to Enhance Delivery of Agents Across the Blood Brain Barrier

Some embodiments provided herein relate to improved compounds, compositions, compounds and methods for delivering therapeutics across the blood brain barrier. In some embodiments, the therapeutic can be a compound that does not easily cross the blood brain barrier, or that does not cross the blood brain barrier at all, e.g., due to hydrophilicity, size, charge, and the like. In some embodiments, the compound can be glycosylated, e.g., include one or more sugars, such as glucose, mannose, fructose, galactose, and the like. In some embodiments, the compound can include an N-linked oligosaccharide, an O-linked oligosaccharide, an α-D glucose linkage, a β-D glucose linkage, an α-D galactose linkage, or a β-D galactose linkage, a mannose linkage, and the like. In some embodiments, the compound comprises a glucose moiety linked via an amide, ester, carbamate, peptide or glycosidic bond.

In some embodiments, the glycosylated compound can be a chemotherapeutic agent, such as chlorambucil, arsenic, cisplatin, fluorouracil, topotecan, carboplatin, imatinib mesylate, erlotinib, all trans-retinoic acid, gemcitabine, sunitinib malate, hydroxyurea, oxaliplatin, estramustine, 2-deoxycoformycin, fludarabine, mitotane, suramin, docetaxel, paclitaxel, cytosine arabinoside, doxorubicin, dacarbazine, temozolamide, vincristine, vinblastine, vinorelbine, fludarabine, cladribine, pentostatin, mitomycin, mitoxantrone, capecitabine, diphenylhydramine, ranitidine, teniposide, etoposide, cytarabine, procarbazine, 6-mercaptopurine, aldesleukin, denileukin, diftitox, interferon α, sorafenib, bortezomib, thalidomide, lenalidomide, ketoconazole, flutamide, estramustine, cyclophosphamide, ifosfamide, interleukin 2, interferon β, interferon γ, adriamycin, and the like, or any combination thereof.

In some embodiments, the compound can a cholinesterase inhibitor, such as donepezil (ARICEPT®); rivastigmine (EXELON®); galantamine (RAZADYNE®); memantine (NAMENDA®); tacrine (COGNEX®); amantiadine; slegiline; levadopa/carbidopa; levodopa/benserazide; entacapone; tolcapone; bromocriptine; pergolide; ropinirole; cabergoline; apomorphine; lisuride; biperiden HCl (AKINETON®); Benzotropine mesylate (COGENTIN®); Procyclidine, trihexyphenidyl; Tetrabenazine (XENAZINE®); clonazepam (KLONOPINAND®); clozapine (CLOZARIL®); nortriptyline (PAMELOR®); Lithium (ESKALITHAND®); selective serotonin reuptake inhibitors, such as Citalopram escitalopram (LEXAPRO®), fluvoxamine (LUVOX®), paroxextine (PAXIL®), fluoxetine (PROZAC®), and sertraline (ZOLOFT®), tricyclic antidepressants, such as Amitriptyline, desipramine, nortriptyline, duloxetine, desvenlafaxine, mirtazepine; monoamine oxidase inhibitors (MAOI's), such as phenelzine (NARDIL®), tranylcypromine (PARNATE®), venlafaxine, buproprioin (WELLBUTRIN®); atypical antipsychotics such as amisulpride, Ariprpazole, asenapine, iloperidone, melperone, olanzapine, paliperidone, perosprione, quetipaine, risperidone, sertindole, sulpride, ziprasizone; antipsychotics such as chlorpromazine, flupehazine, haloperidol, moindone, thiothixene, thioridazine, trifluoperazine, loxaine, perphenazine, prochlorperazine, pimozide, auclopenthixol, Ritalin, methyline, metadata, focalin, dayrana, concerta, adderall, Dexedrine, vyvanse, clonidine (CATAPRES®), guanfacine (TENEX®); atomoxetine (STRATTERA®), diphenylhydramine, doxylamine, estazolam, flurazapam, quazepam, temazepam, triazolam, oxazepam, prazepam, alprazolam, fluritrazepam, trimipramine, eszopiclone, zalepon, zolpidem, rameliteon, trazodone, memanitine, vitamin E, a phospholipid or an omega-3 fatty acid, and the like, or any combination thereof.

In some embodiments, the methods include providing a therapeutically effective amount of an agent that targets the brain and/or central nervous system, and providing a therapeutically effective amount of chromium. The chromium can provided to the subject in an amount effective to enhance or increase GLUT1 and/or GLUT3 levels in the brain, or a therapeutically effective amount, as described herein, and preferably between about amount between about 0.001 μg to about 10 g.

In some embodiments, the chromium and the agent that targets the brain and/or the central nervous system can be provided in a single dosage form, e.g., a single tablet, a single infusion, etc. In some embodiments, the chromium and the agent can be provided sequentially, in separate dosage forms, as described herein. Preferably, the chromium and the agent are administered substantially simultaneously.

In some embodiments, the chromium is administered to the subject 1 time, 2 times, 3 times, 4 times 5 times, 6 times, 7 times, 8 times, 9 times, 10 times, or more, per day, for a period of time, such as 1 day, 2 days, 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 2 months, 3 months, 4 months, 5 months, 6 months, 7 months, 8 months, 9 months, 10 months, 11 months, 1 year, or more, or any amount of time in between the preceding values, prior to administration, or during the administration of the agent that targets the brain and/or central nervous system.

Compositions

Some embodiments provided herein relate to compositions that comprise, consist essentially of, or consist of a therapeutically effective amount of chromium and a therapeutically effective amount of an agent that targets the brain and/or central nervous system. As used herein, the phrase "agent that targets the brain and/or central nervous system" refer to agents having a site of action within the brain or central nervous system, including agents that must cross the blood brain barrier.

Examples of agents that target the brain and/or central nervous system include, without limitation, chemotherapeutics for intracerebral tumors, e.g., chorambucil, arsenic, cisplatin, fluorouracil, topotecan, carboplatin, imatinib mesylate, erlotinib, all trans-retinoic acid, gemcitabine, sunitinib malate, hydroxyurea, oxaliplatin, estramustine, 2-deoxycoformycin, fludarabine, mitotane, suramin, docetaxel, paclitaxel, cytosine arabinoside, doxorubicin, dacarbazine, temozolamide, vincristine, vinblastine, vinorelbine, fludarabine, cladribine, pentostatin, mitomycin, mitoxantrone, capecitabine, diphenylhydramine, ranitidine, teniposide, etoposide, cytarabine, procarbazine, 6-mercaptopurine, aldesleukin, denileukin, diftitox, interferon α, sorafenib, bortezomib, thalidomide, lenalidomide, ketoconazole, flutamide, estramustine, cyclophosphamide, ifosfamide, interleukin 2, interferon β, interferon γ, adriamycin, and the like, or any combination thereof.

Other agents that target the brain or central nervous system include, without limitation antidepressants, antipsychotics, sleep aids, and therapeutics for cognitive conditions and disorders provided herein, including but not limited to cholinesterase inhibitors, such as donepezil (ARICEPT®); rivastigmine (EXELON®); galantamine (RAZADYNE®); memantine (NAMENDA®); tacrine (COGNEX®); amantiadine; slegiline; levadopa/carbidopa; levodopa/benserazide; entacapone; tolcapone; bromocriptine; pergolide; ropinirole; cabergoline; apomorphine; lisuride; biperiden HCl (AKINETON®); Benzotropine mesylate (COGENTIN®); Procyclidine, trihexyphenidyl; Tetrabenazine (XENAZINE®); clonazepam (KLONOPINAND®); clozapine (CLOZARIL®); nortriptyline (PAMELOR®); Lithium (ESKALITHAND®); selective serotonin reuptake inhibitors, such as Citalopram escitalopram (LEXAPRO®), fluvoxamine (LUVOX®), paroxextine (PAXIL®), fluoxetine (PROZAC®), and sertraline (ZOLOFT®), tricyclic antidepressants, such as Amitriptyline, desipramine, nortriptyline, duloxetine, desvenlafaxine, mirtazepine; monoamine oxidase inhibitors (MAOI's), such as phenelzine (NARDIL®), tranylcypromine (PARNATE®); venlafaxine, buproprioin (WELLBUTRIN®);

atypical antipsychotics such as amisulpride, Ariprpazole, asenapine, iloperidone, melperone, olanzapine, paliperidone, perosprione, quetipaine, risperidone, sertindole, sulpride, ziprasizone; antipsychotics such as chlorpromazine, flupehazine, haloperidol, moindone, thiothixene, thioridazine, trifluoperazine, loxaine, perphenazine, prochlorperazine, pimozide, auclopenthixol, Ritalin, methyline, metadata, focalin, dayrana, concerta, adderall, Dexedrine, vyvanse, clonidine (CATAPRES®), guanfacine (TENEX®); atomoxetine (STRATTERA®), diphenylhydramine, doxylamine, estazolam, flurazepam, quazepam, temazepam, triazolam, oxazepam, prazepam, alprazolam, fluritrazepam, trimipramine, eszopiclone, zalepon, zolpidem, rameliteon, trazodone, memanitine, vitamin E, a phospholipid or an omega-3 fatty acid and the like, or any combination thereof.

Having now generally described the invention, the same will become better understood by reference to certain specific examples which are included herein for purposes of illustration only and are not intended to be limiting unless other wise specified. All referenced publications and patents are incorporated by reference herein, for the material specifically referred to herein and in their entirety.

EXAMPLES

Example 1

Chromium Increases Brain Glucose Transporter Levels in Subjects with Obesity and/or Insulin Resistance In order to test whether chromium affected insulin-resistance induced decreases in brain glucose transporter GLUT1 and GLUT3 levels, the levels of GLUT1 and GLUT3 expression products were compared in insulin-resistant or hyperglycemic animals, with and without administration of chromium.

Briefly, insulin resistance and hyperglycemia were induced in male Wistar rats by feeding a high fat diet (HFD, 40% of calories as fat). A healthy control group received a standard diet (12% of calories as fat). Rats were fed their diets throughout the 12 week study.

Rats (10/group) were divided into groups: healthy control (Control), HFD, and HFD+CrHis. Chromium (Cr) treated rats were fed CrHis (110 mcg/kg body wt/d). Cr treatment started at the beginning of the study and was continued for 12 weeks. After 12 weeks, chromium levels and GLUT-1 and GLUT-3 expression (Western blot analysis) were measured from brain tissue homogenates. Body weight, serum chromium levels, and blood glucose levels were also measured.

The study results are shown in Table 1. Rats fed a high fat diet had significantly decreased levels of chromium in the brain, as compared to control (−26%). The levels of GLUT-1 (−38%) and GLUT-3 (−11.2%) were also significantly decreased compared to control. Rats fed the high fat diet also had significantly increased body weight (+14%), increased blood glucose levels (+30%), and decreased serum chromium levels (−20%) as compared to control.

Addition of chromium histidinate to the high fat diet significantly increased brain and serum chromium levels, increased brain GLUT-1 and GLUT-3 levels, and decreased body weight and blood glucose levels, compared to the high fat diet alone. The data are presented in TABLE 1, below, and in FIG. 1.

TABLE 1

Comparison of efficacy variables after treatment (mean ± s.e.m.)

| | Control | HFD | HFD + CrHis |
|---|---|---|---|
| Body Weight (g) | 288.7 ± 3.0$^a$ | 329.2 ± 1.3$^b$ | 315.1 ± 1.9$^c$ |
| Blood Glucose (mg/dL) | 101.5 ± 1.6$^a$ | 132.3 ± 2.3$^b$ | 116.4 ± 2.1$^c$ |
| Serum Chromium (ng/g) | 16.9 ± 0.4$^a$ | 13.6 ± 0.3$^b$ | 22.0 ± 0.6$^c$ |
| Brain Chromium (ng/g) | 15.6 ± 0.3$^a$ | 11.2 ± 0.2$^b$ | 17.7 ± 0.2$^c$ |
| GLUT-1 (% of Control) | 100.0 ± 1.2$^a$ | 62 ± 1.5$^b$ | 89.5 ± 0.3$^c$ |
| GLUT-3 (% of Control) | 100.0 ± 0.6$^a$ | 88.8 ± 3.8$^b$ | 106.3 ± 1.5$^a$ |

Different letters represent statistical significance (p < 0.01) between groups.

The data above demonstrate that chromium administration can enhance brain GLUT-1 and GLUT-3 expression. Further, the data show that the enhancement is independent of insulin, and is observed even in insulin resistant subjects. As such, chromium provides a powerful supplement useful in the treatment, management, or prevention of diseases or disorders associated with altered cerebral glucose metabolism. This result was unexpected, as neither GLUT1 nor GLUT3 has been shown to be influenced by insulin. This study also shows that a high fat diet decreases brain chromium levels, and brain GLUT-1 and GLUT-3 levels.

Example 2

Chromium Increases Brain Glucose Transporter Levels in Subjects with Diabetes and/or Insulin Resistance In order to test whether chromium affected diabetes-induced decreases in brain glucose transporter GLUT1 and GLUT3 levels, the levels of GLUT1 and GLUT3 expression products were compared between healthy control animals and animals with type 2 diabetes; with and without administration of chromium.

An animal model of type 2 diabetes was produced by feeding male Sprague-Dawley rats (n=10) with a high-fat diet (HFD, 40% Kcal from fat) for 2 weeks, then intraperitoneally administering streptozotocin (STZ, 40 mg/kg). The HFD-treated rats and the HFD/STZ-treated rats were then administered 80 µg chromium picolinate/kg body weight/day for 12 weeks. Chromium picolinate was obtained from Nutrition 21, Purchase, N.Y. Untreated Sprague-Dawley (standard control diet) and HFD/STZ-treated rats not administered chromium served as controls.

After 12 weeks, chromium levels and GLUT-1 and GLUT-3 expression (Western blot analysis) were measured from brain tissue homogenates.

Addition of chromium to the diets of the diabetic rats significantly increased brain and serum chromium levels, increased brain GLUT-1 and GLUT-3 levels, compared to the groups not administered chromium. The data are shown graphically in FIG. 2.

Example 3

A subject is identified as having GLUT1 deficiency syndrome. The subject presents with one or more symptoms associated with GLUT1 deficiency syndrome such as the presence of a SLC2A1 mutation, neurological problems associated with GLUT1 deficiency such as stiffness caused by abnormal tensing of the muscles (spasticity), difficulty in coordinating movements (ataxia), and speech difficulties (dysarthria). The subject can experience episodes of confusion, lack of energy (lethargy), headaches, muscle twitches (myoclonus), or involuntary irregular eye movements, particularly before meals.

The subject is administered between 50 µg and 5000 µg chromium histidinate, chromium picolinate, or chromium histidinate/chromium picolinate combination complex/day. The chromium histidinate is administered orally. After a period of time, a reduction in one or more of the symptoms of GLUT1 deficiency is observed.

Example 4

A subject is identified as having early stage Alzheimer's disease. The subject presents with one or more symptoms including memory changes that disrupt daily life, challenges in planning or solving problems, difficulty in completing familiar tasks, confusion with time or place, trouble understanding visual images and spatial relationships, new problems with words in speaking or writing, misplacing things and losing the ability to retrace steps, decreased or poor judgment, withdrawal from work or social activity, and changes in mood and personality.

The subject is administered between 50 µg and 5000 µg chromium provided as a combination of chromium picolinate and chromium histidinate. The chromium is administered orally. The subject's condition, as assessed by one or more symptoms of the disease, does not worsen, or improves, over time.

Example 5

A subject is identified as having Alzheimer's disease by a routine dementia screening test, such as a clock drawing test, a time and change test, a sniff test, or the like, and/or shows symptoms of Alzheimer's as evidenced by a PET scan.

The subject is administered between 50 µg and 5000 µg chromium as chromium nicotinate, chromium picolinate, or a combination of chromium picolinate and chromium histidinate, in conjunction with one or more standard therapeutics for Alzheimer's disease. The chromium is administered orally. The subject's condition, as assessed by one or more symptoms of the disease, does not worsen or improves over a period of five days Example 6

A subject is identified as having Parkinson's disease by conventional methods.

The subject is administered between 50 µg and 5000 µg chromium polyhistidinate. The chromium is administered orally. The subject's condition, as assessed by one or more symptoms of the disease, does not worsen or improves over time.

Example 7

A subject is identified as having mild cognitive impairment by conventional methods.

The subject is administered between 50 µg and 5000 µg chromium complex. The chromium is administered orally. The subject's condition, as assessed by one or more symptoms of the condition, does not worsen over time.

Example 8

A subject presents with symptoms of Alzheimer's. The subject is administered between 50 µg and 5000 µg chromium complex, and a derivative of L-dopa or dopamine linked through a succinic acid spacer to either the C-3 position of glucose or the C-6 position of mannose.

The subject's condition, as assessed by one or more symptoms of the condition, improves over time.

Example 9

A subject presents with symptoms of ADHD. The subject is administered between 50 µg and 5000 µg chromium complex, and a derivative of Ritalin bearing a glucose substituent, e.g., on its phenyl ring.

The subject's condition, as assessed by one or more symptoms of the condition, improves over time.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of enhancing glucose transporters in the brain of a subject in need thereof, comprising:
    identifying a subject in need of increased glucose transport in the brain; and
    administering to a subject in need thereof an amount of chromium effective to increase the levels of GLUT-1 or GLUT-3 in the brain.

2. The method of claim 1, wherein the chromium is a chromium complex.

3. The method of claim 1, wherein the subject is human.

4. The method of claim 3, wherein the subject has a disease or disorder associated with a decreased level of glucose transporters in the brain.

5. The method of claim 4, wherein the disease or disorder is selected from the group consisting of: Alzheimer's disease, dementia, mild cognitive impairment (MCI), attention deficit hyperactive disorder (ADHD), Huntington's Disease, epilepsy, and Parkinson's Disease.

6. The method of claim 2, wherein the chromium complex comprises chromium histidinate.

7. The method of claim 6, wherein the chromium complex further comprises chromium picolinate.

8. The method of claim 2, wherein the chromium complex consists essentially of chromium histidinate and chromium picolinate.

* * * * *

UNITED STATES PATENT AND TRADEMARK OFFICE
CERTIFICATE OF CORRECTION

PATENT NO.          : 9,028,879 B2
APPLICATION NO.     : 13/380940
DATED               : May 12, 2015
INVENTOR(S)         : James R. Komorowski It is certified that error appears in the above-identified patent and that said Letters Patent is hereby corrected as shown below:

On the Title Page

In column 2 (page 1, item 56) at line 3, Under U.S. Patent Documents, change "GLUTI" to --GLUT1--.

In The Specification

In column 2 at line 3, Change "27(10" to --27(11--.

In column 2 at line 40, Change "and or" to --and/or--.

In column 2 at line 40, Change "and or" to --and/or--.

In column 2 at line 41, Change "and or" to --and/or--.

In column 5 at line 39, Change "epilepsiapartialis" to --epilepsia partialis--.

In column 8 at lines 10-11, Change "hyperinsulinemia" to --hyperinsulinemia.--.

In column 9 at line 10, Change "and or" to --and/or--.

In column 10 at line 9, Change "5-hydroxytrytophan," to --5-hydroxytryptophan,--.

In column 10 at line 44, Change "Groffonia" to --Griffonia--.

In column 11 at line 63, Change "memanitine," to --memantine,--.

In column 12 at line 12, Change "amantiadine;" to --amantadine;--.

In column 12 at line 12, Change "slegiline" to --selegiline--.

In column 12 at line 12, Change "levadopa" to --levodopa--.

In column 12 at line 15, Change "Benzotropine" to --Benztropine--.

In column 12 at lines 17-18, Change "(KLONOPINAND®);" to --(KLONOPIN®);--.

In column 12 at line 19, Change "(ESKALITHAND®);" to --(ESKALITH®);--.

In column 12 at line 21, Change "paroxextine" to --paroxetine--.

In column 12 at line 24, Change "mirtazepine;" to --mirtazapine;--.

In column 12 at line 27, Change "buproprioin" to --bupropion--.

Signed and Sealed this
Twenty-second Day of March, 2016

Michelle K. Lee
*Director of the United States Patent and Trademark Office*

In column 12 at line 28, Change "Ariprpazole," to --Aripiprazole,--.

In column 12 at line 29, Change "perosprione," to --perospirone,--.

In column 12 at lines 29-30, Change "quetipaine," to --quetiapine,--.

In column 12 at line 30, Change "sulpride," to --sulpiride,--.

In column 12 at line 30, Change "ziprasizone;" to --ziprasidone;--.

In column 12 at line 31, Change "flupehazine," to --fluphenazine,--.

In column 12 at line 32, Change "loxaine," to --loxapine,--.

In column 12 at line 34, Change "methyline," to --methylene,--.

In column 12 at line 34, Change "dayrana," to --daytrana,--.

In column 12 at line 37, Change "memanitine," to --memantine,--.

In column 12 at line 40, Change "antispychotic" to --antipsychotic--.

In column 15 at line 6, Change "sialastic" to --silastic--.

In column 15 at line 8, Change "tissue" to --tissue.--.

In column 17 at lines 13-14, Change "temozolamide," to --temozolomide,--.

In column 17 at line 16, Change "diphyenylhydramine," to --diphenylhydramine,--.

In column 17 at line 26, Change "amantiadine;" to --amantadine;--.

In column 17 at line 26, Change "slegiline" to --selegiline--.

In column 17 at line 27, Change "levadopa" to --levodopa--.

In column 17 at lines 29-30, Change "Benzotropine" to --Benztropine--.

In column 17 at line 32, Change "(KLONOPINAND®);" to --(KLONOPIN®);--.

In column 17 at line 33, Change "(ESKALITHAND®);" to --(ESKALITH®);--.

In column 17 at line 36, Change "paroxextine" to --paroxetine--.

In column 17 at line 39, Change "mirtazepine;" to --mirtazapine;--.

In column 17 at line 41, Change "buproprioin" to --bupropion--.

In column 17 at line 42, Change "Ariprpazole," to --Aripiprazole,--.

In column 17 at line 44, Change "perosprione," to --perospirone,--.

In column 17 at line 44, Change "quetipaine," to --quetiapine,--.

In column 17 at line 44, Change "sulpride," to --sulpiride,--.

In column 17 at line 45, Change "ziprasizone" to --ziprasidone--.

In column 17 at lines 45-46, Change "flupehazine," to --fluphenazine,--.

In column 17 at line 47, Change "loxaine," to --loxapine,--.

In column 17 at line 48, Change "methyline," to --methylene,--.

In column 17 at line 49, Change "dayrana," to --daytrana,--.

In column 17 at line 52, Change "flurazapam," to --flurazepam,--.

In column 17 at line 53, Change "fluritrazepam," to --flunitrazepam,--.

CERTIFICATE OF CORRECTION (continued)
U.S. Pat. No. 9,028,879 B2

In column 17 at line 54, Change "zalepon," to --zaleplon,--.

In column 17 at line 54, Change "rameliteon," to --ramelteon,--.

In column 17 at line 55, Change "memanitine," to --memantine,--.

In column 18 at line 31, Change "chorambucil," to --chlorambucil,--.

In column 18 at lines 36-37, Change "temozolamide," to --temozolomide,--.

In column 18 at line 39, Change "diphyenylhydramine," to --diphenylhydramine,--.

In column 18 at lines 52-53, Change "amantiadine;" to --amantadine;--.

In column 18 at line 53, Change "slegiline" to --selegiline--.

In column 18 at line 53, Change "levadopa" to --levodopa--.

In column 18 at line 56, Change "Benzotropine" to --Benztropine--.

In column 18 at line 58, Change "(KLONOPINAND®);" to --(KLONOPIN®);--.

In column 18 at line 59, Change "(ESKALITHAND®);" to --(ESKALITH®);--.

In column 18 at lines 61-62, Change "paroxextine" to --paroxetine--.

In column 18 at line 65, Change "mirtazepine;" to --mirtazapine;--.

In column 18 at line 67, Change "buproprioin" to --bupropion--.

In column 19 at line 1, Change "Ariprpazole," to --Aripiprazole,--.

In column 19 at line 3, Change "perosprione," to --perospirone,--.

In column 19 at line 3, Change "quetipaine," to --quetiapine,--.

In column 19 at line 3, Change "sulpride," to --sulpiride,--.

In column 19 at line 4, Change "ziprasizone;" to --ziprasidone;--.

In column 19 at lines 4-5, Change "flupehazine," to --fluphenazine,--.

In column 19 at line 6, Change "loxaine," to --loxapine,--.

In column 19 at line 7, Change "methyline," to --methylene,--.

In column 19 at line 8, Change "dayrana," to --daytrana,--.

In column 19 at line 11, Change "flurazapam," to --flurazepam,--.

In column 19 at line 12, Change "fluritrazepam," to --flunitrazepam,--.

In column 19 at line 13, Change "zalepon," to --zaleplon,--.

In column 19 at line 13, Change "rameliteon," to --ramelteon,--.

In column 19 at line 14, Change "memanitine," to --memantine,--.

In column 21 at line 43, Change "days" to --days.--.

In The Claims

In column 22 at lines 36-37 (approx.), In Claim 1, after "comprising:" delete "identifying a subject in need of increased glucose transport in the brain; and".